United States Patent
Shimizu et al.

(10) Patent No.: US 12,097,070 B2
(45) Date of Patent: Sep. 24, 2024

(54) IMAGING DEVICE

(71) Applicant: TERUMO KABUSHIKI KAISHA, Tokyo (JP)

(72) Inventors: Katsuhiko Shimizu, Fujinomiya (JP); Yasukazu Sakamoto, Hiratsuka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 684 days.

(21) Appl. No.: 17/037,019

(22) Filed: Sep. 29, 2020

(65) Prior Publication Data

US 2021/0007580 A1     Jan. 14, 2021

Related U.S. Application Data

(63) Continuation of application No. PCT/JP2019/011691, filed on Mar. 20, 2019.

(30) Foreign Application Priority Data

Mar. 29, 2018   (JP) ................................ 2018-064012

(51) Int. Cl.
    *A61B 8/00*         (2006.01)
    *A61B 1/00*         (2006.01)
               (Continued)

(52) U.S. Cl.
    CPC ........ *A61B 8/0883* (2013.01); *A61B 1/00009* (2013.01); *A61B 1/126* (2013.01);
               (Continued)

(58) Field of Classification Search
    None
    See application file for complete search history.

(56) References Cited

U.S. PATENT DOCUMENTS

| | | |
|---|---|---|
| 2013/0023770 A1 | 1/2013 | Courtney et al. |
| 2014/0371598 A1 | 12/2014 | Okubo et al. |
| | (Continued) | |

FOREIGN PATENT DOCUMENTS

| | | |
|---|---|---|
| CN | 106102545 A | 11/2016 |
| JP | 2002-200081 A | 7/2002 |
| | (Continued) | |

OTHER PUBLICATIONS

English Translations of the International Search Report (Form PCT/ISA/210) and the Written Opinion of the International Searching Authority (Form PCT/ISA/237) issued Jun. 18, 2019, by the Japanese Patent Office in corresponding International Application No. PCT/JP2019/011691. (8 pages).

(Continued)

*Primary Examiner* — Shahdeep Mohammed
(74) *Attorney, Agent, or Firm* — BUCHANAN INGERSOLL & ROONEY PC

(57) ABSTRACT

An imaging device capable of acquiring images of an internal structure of a living body highly accurately in a wide range. An imaging device has a first housing to which a proximal portion of an outer sheath is fixed, with a drive shaft for driving a imaging unit and an inner sheath extending through the first housing, and a second housing to which a proximal portion of the inner sheath is fixed and which holds the drive shaft rotatably therein. The first housing has a first port held in fluid communication with an inner lumen of the outer sheath, and the second housing is movable toward and away from the first housing. The imaging device also includes a first gap between the inner sheath and the outer sheath and a second gap between the inner sheath and the drive shaft.

20 Claims, 5 Drawing Sheets

(51) Int. Cl.
  *A61B 1/12*    (2006.01)
  *A61B 8/08*    (2006.01)
  *A61B 8/12*    (2006.01)
  *A61M 25/00*   (2006.01)
  *A61M 39/00*   (2006.01)

(52) U.S. Cl.
  CPC ............ *A61B 8/4281* (2013.01); *A61B 8/445* (2013.01); *A61M 25/0082* (2013.01); *A61B 8/12* (2013.01); *A61B 8/4461* (2013.01); *A61B 8/483* (2013.01); *A61M 2039/0018* (2013.01)

(56) References Cited

U.S. PATENT DOCUMENTS

| | | |
|---|---|---|
| 2016/0022244 A1 | 1/2016 | Courtney et al. |
| 2016/0367231 A1 | 12/2016 | Uemichi et al. |
| 2017/0079616 A1 | 3/2017 | Yamamoto |
| 2017/0333001 A1 | 11/2017 | Sakaguchi |
| 2020/0046202 A1* | 2/2020 | Morishima .......... A61B 1/0051 |

FOREIGN PATENT DOCUMENTS

| | | |
|---|---|---|
| JP | 2002253551 A | 9/2002 |
| JP | 2004305334 A | 11/2004 |
| JP | 2016512708 A | 5/2016 |
| JP | 6073295 B2 | 1/2017 |
| JP | 2017056156 A | 3/2017 |
| WO | 2012/162829 A1 | 12/2012 |
| WO | 2013/133356 A1 | 9/2013 |

OTHER PUBLICATIONS

International Search Report (PCT/ISA/210) mailed on Jun. 18, 2019, by the Japanese Patent Office as the International Searching Authority for International Application No. PCT/JP2019/011691.
Written Opinion (PCT/ISA/237) mailed on Jun. 18, 2019, by the Japanese Patent Office as the International Searching Authority for International Application No. PCT/JP2019/011691.
Office Action (The First Office Action) issued Mar. 1, 2023, by the National Intellectual Property Administration, P. R. China in corresponding Chinese Patent Application No. 201980022746.3 and an English translation of the Office Action. (11 pages).
The extended European Search Report issued Apr. 1, 2021, by the European Patent Office in corresponding European Patent Application No. 19775685.1-1126. (7 pages).

* cited by examiner

IMAGING DEVICE

CROSS-REFERENCES TO RELATED APPLICATIONS

This application is a continuation of International Application No. PCT/JP2019/011691 filed on Mar. 20, 2019, which claims priority to Japanese Application No. 2018-064012 filed on Mar. 29, 2018, the entire content of both of which is incorporated herein by reference.

FIELD OF THE DISCLOSURE

The present disclosure generally relates to an imaging device and more particularly to an imaging device for acquiring images by being inserted into a lumen such as a blood vessel or a duct.

BACKGROUND DISCUSSION

In a case where a lesion in a lumen in a living body such as a blood vessel or a duct is to be examined, an imaging device can be inserted into the lumen in the living body for acquiring images of the lesion by using ultrasonic waves or light. For example, an imaging device using ultrasonic waves includes a vibrator for sending and receiving ultrasonic waves, a drive shaft for rotating the vibrator, and a sheath in which the vibrator and the drive shaft are rotatably housed. The vibrator sends and receives ultrasonic waves while the vibrator is rotated by the drive shaft in the sheath, for acquiring a three-dimensional image in a living body. An imaging device capable of moving a vibrator along a central axis in an outer sheath can be used for observing a blood vessel such as a coronary artery.

Obtaining a three-dimensional perception of the internal structure of a heart is important for working out a therapeutic strategy for the heart. However, heart chambers are rather large compared to coronary arteries or the like. When an imaging device for use in coronary arteries or the like is inserted into a heart chamber, since the vibrator is relatively small, ultrasonic waves generated may possibly fail to spread over sufficient distances. Consequently, for acquiring images in a large space such as a heart chamber, it is desirable to increase the area of the vibrator. The increased area of the vibrator allows generated ultrasonic waves to spread over longer distances.

However, when an imaging device is inserted into a large space such as a heart chamber, the imaging device is liable to move freely. Especially in a case where the vibrator has an increased size, when the vibrator is actuated in the sheath, the position of a distal portion of the imaging device tends to be unstable. Therefore, it may be difficult for the imaging device to accurately and stably acquire three-dimensional images of a large internal structure such as a heart.

In addition, the imaging device using ultrasonic waves is usually required to remove air from the sheath in which the vibrator is positioned. With the sheath filled up with saline (i.e., saline solution), ultrasonic waves generated or detected by the vibrator can efficiently be propagated through the sheath. For example, Japanese Patent No. 6073295 discloses a device in which a housing positioned proximal to a sheath with a vibrator disposed in the housing has a main port and an auxiliary port. A fluid supplied from the main port to the housing flows through the sheath and reaches the vibrator. Thereafter, the fluid flows through the sheath back to the housing from which the fluid is drained through the auxiliary port. The device disclosed in Japanese Patent No. 6073295 is therefore able to remove air without discharging the fluid from the distal portion of the sheath into the living body.

According to the device disclosed in Japanese Patent No. 6073295, the vibrator is unable to move along the central axis in the sheath. Consequently, it is difficult for the device to acquire images of the internal structure of a living body highly accurately in a three-dimensionally wide range.

SUMMARY

An imaging device that is capable of acquiring images of the internal structure of a living body highly accurately in a wide range.

In accordance with an aspect, an imaging device is disclosed, which includes an elongated outer sheath, an imaging unit disposed in the outer sheath, a drive shaft to which the imaging unit is fixed at a distal portion, the drive unit configured to transmit drive power to the imaging unit in the outer sheath, an inner sheath configured to be movable along a central axis of the outer sheath in the outer sheath, the drive shaft extending through the inner sheath, a first housing to which a proximal portion of the outer sheath is fixed, the drive shaft and the inner sheath extending through the first housing, a second housing is disposed proximal to the first housing and to which a proximal portion of the inner sheath is fixed, the drive shaft being rotatably held in the second housing, a first gap between the inner sheath and the outer sheath, and a second gap between the inner sheath and the drive shaft. The first gap and the second gap are held in fluid communication with each other on a distal side of the inner sheath, the first housing has a first port held in fluid communication with the first gap, and the second housing is configured to be movable toward and away from the first housing and includes a second port held in fluid communication with the second gap.

In accordance with another aspect, an imaging device is disclosed comprising: an elongated outer sheath; an imaging unit disposed in the outer sheath; a drive shaft to which the imaging unit is fixed at a distal portion of the drive shaft, the drive shaft configured to transmit drive power to the imaging unit in the outer sheath; an inner sheath configured to be movable along a central axis of the outer sheath in the outer sheath, the drive shaft extending through the inner sheath; a first housing to which a proximal portion of the outer sheath is fixed, the drive shaft and the inner sheath extending through the first housing; a second housing that is disposed proximal to the first housing and to which a proximal portion of the inner sheath is fixed, the drive shaft being rotatably held in the second housing; a first gap between the inner sheath and the outer sheath; a second gap between the inner sheath and the drive shaft, wherein the first housing has a first port held in fluid communication with the first gap; the second housing configured to be movable toward and away from the first housing and includes a second port held in fluid communication with the second gap; the inner sheath including a distal opening at a distal end of the inner sheath, the distal opening held in fluid communication with the second gap; the imaging unit being disposed apart from the distal opening of the inner sheath to define a third gap between the imaging unit and the distal opening of the inner sheath, the third gap held in fluid communication with the first gap and the second gap; and when the second housing moves toward and away from the first housing, the inner sheath moves with the imaging unit along the central axis of the outer sheath in the outer sheath while keeping the third gap.

In accordance with a further aspect, a method of removing air from an imaging device is disclosed, the method comprising: introducing a saline solution into a proximal side of the imaging device, the image device including an elongated outer sheath, an imaging unit disposed in the outer sheath, a drive shaft to which the imaging unit is fixed at a distal portion of the drive shaft, the drive shaft configured to transmit drive power to the imaging unit in the outer sheath, an inner sheath configured to be movable along a central axis of the outer sheath in the outer sheath, the drive shaft extending through the inner sheath, a first gap between the outer sheath and the inner sheath, and a second gap between the inner sheath and the drive shaft; flowing the saline solution in the second gap between the inner sheath and the drive shaft from the proximal side of the imaging device towards a distal side of the imaging device; and filling a space between the outer sheath and the imaging unit with the saline solution from the second gap between the inner sheath and the drive shaft to remove the air from the imaging device.

The imaging device constructed as described above allows the imaging unit and the inner sheath to be moved along the central axis of the outer sheath in the outer sheath while being kept at a constant distance from each other. Since the imaging unit can be moved stably, the imaging device is therefore able to acquire images in a wide range and to acquire highly accurate images.

BRIEF DESCRIPTION OF THE DRAWINGS

FIGS. 3A and 3B are a cross-sectional views of the imaging device before an imaging unit of the imaging device is pulled back, and wherein FIG. 3A illustrates a distal part of the imaging device and FIG. 3B illustrates a proximal part of the imaging device.

FIGS. 5A and 5B are a cross-sectional views of the imaging device when the imaging unit of the imaging device is pulled back, and wherein FIG. 3A illustrates the distal part of the imaging device and FIG. 3B illustrates the proximal part of the imaging device.

DETAILED DESCRIPTION

Figure 1:
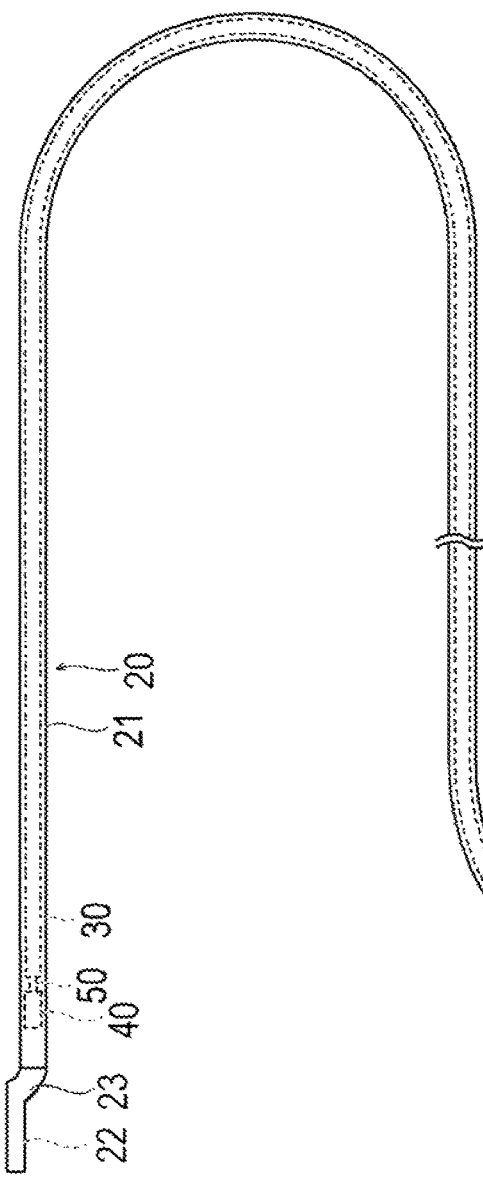
FIG. 1 is a plan view of an imaging device according to an embodiment of the invention.
Figure 1:
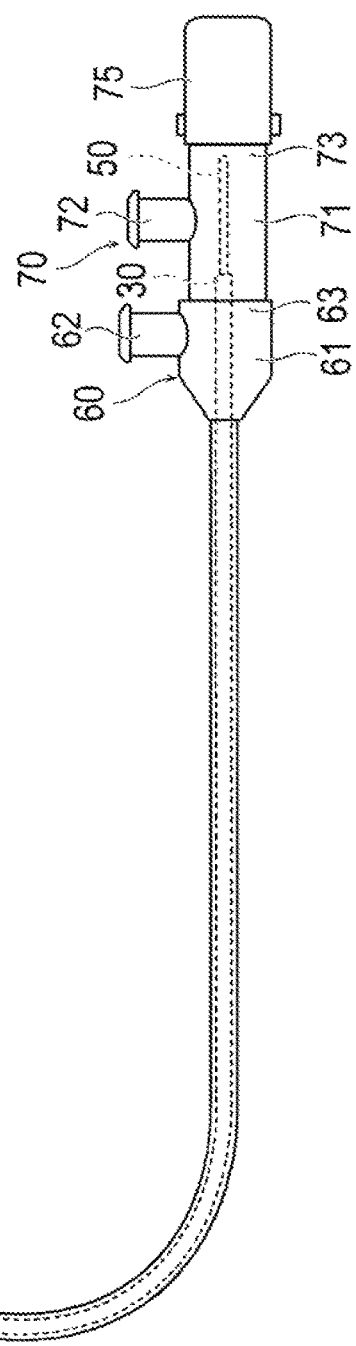

Set forth below with reference to the accompanying drawings is a detailed description of embodiments of an imaging device and more particularly to an imaging device for acquiring images by being inserted into a lumen such as a blood vessel or a duct representing examples of the inventive imaging device. Note that since embodiments described below are preferred specific examples of the present disclosure, although various technically preferable limitations are given, the scope of the present disclosure is not limited to the embodiments unless otherwise specified in the following descriptions. Moreover, in the drawings, the same reference signs are assigned to the same components, and detailed descriptions of the same reference signs assigned to the same components are appropriately omitted. Note that dimensional ratios in the drawings may be depicted as exaggerated and may be different form actual ratios for illustrative purposes.

An imaging device 10 according to the present embodiment is a device mainly for capturing three-dimensional images of a heart or a blood vessel by being inserted into a heart chamber or the blood vessel. Note that, in the present description, the side of the imaging device 10 which is to be inserted into a lumen in a living body will be referred to as a "distal side," whereas the operator side of the imaging device 10 will be referred to as a "proximal side."

Figure 3A:
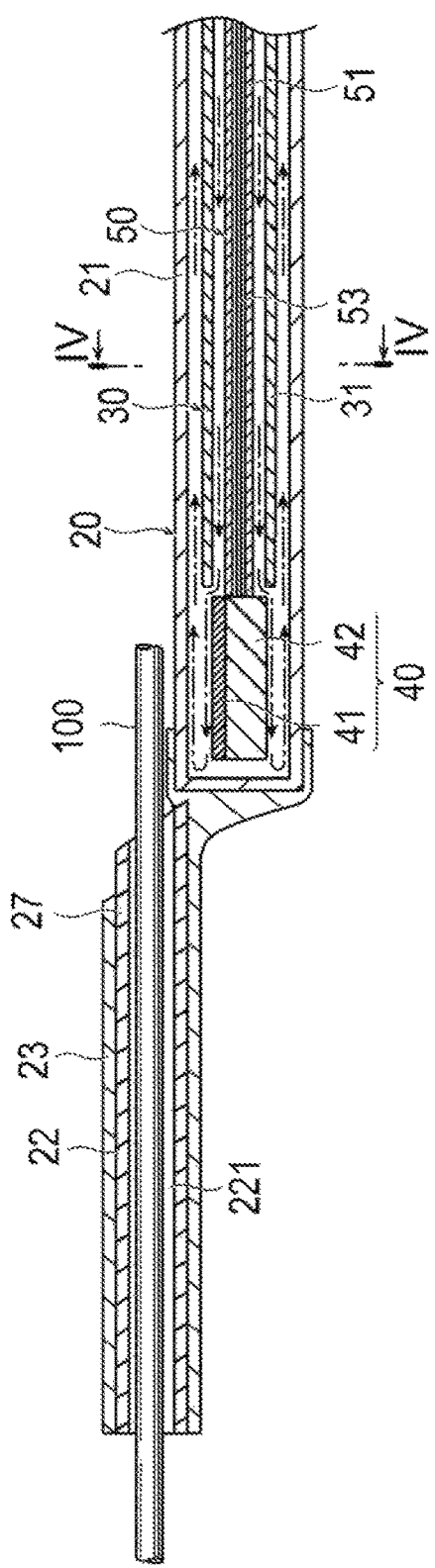
Figure 3B:
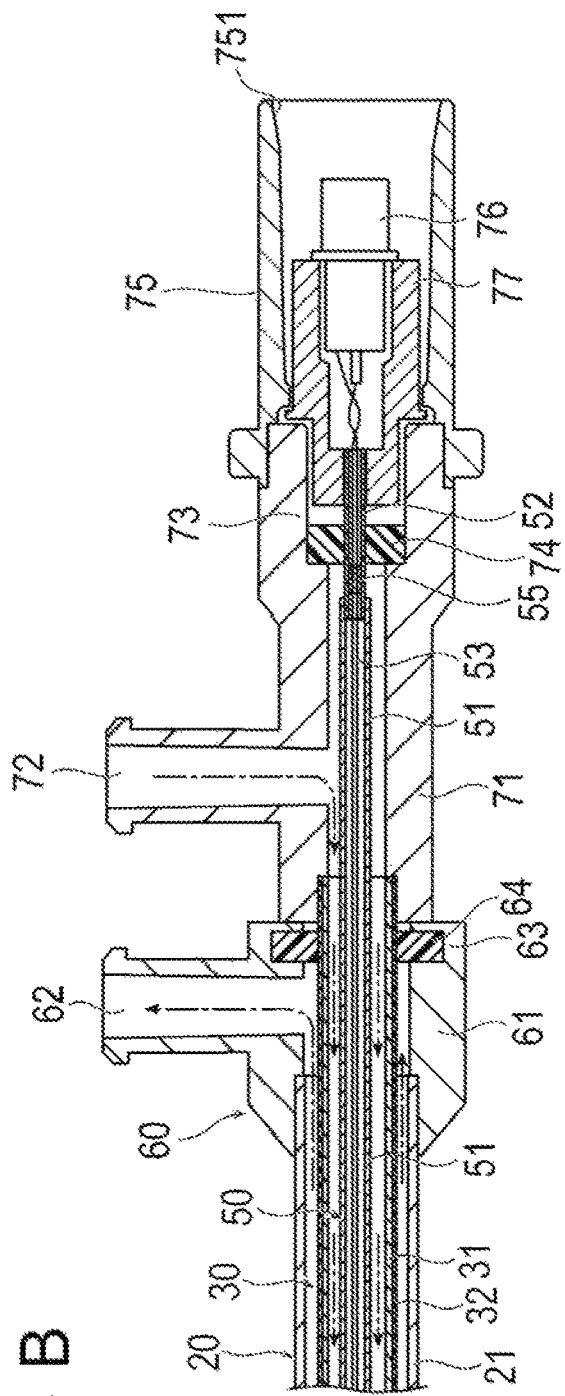

As illustrated in FIGS. 1, 3A, and 3B, the imaging device 10 includes an outer sheath 20, an inner sheath 30, a vibrator unit 40 (i.e., an image acquiring portion), and a drive shaft 50. The imaging device 10 further includes a first housing 60 and a second housing 70.

The outer sheath 20 is a tubular body configured to be inserted into a lumen in a living body. The outer sheath 20 includes an outer sheath body 21, a distal tube 22, and a joint tube 23.

The distal tube 22 is a tubular body in which a guide wire lumen 221 is disposed. A guide wire 100 that has been inserted in a lumen in a living body in advance extends through the guide wire lumen 221. In accordance with an embodiment, the imaging device 10 is of the "rapid exchange type" in which the guide wire lumen 221 is disposed only in a distal portion of the imaging device 10. The guide wire lumen 221 has an opening in a proximal side of the guide wire lumen 221 that is positioned farther on the distal side than the vibrator unit 40. Therefore, the guide wire lumen 221 does not exist in the imaging range of the vibrator unit 40. Consequently, an imaging process is not interfered with by the guide wire lumen 221. Since the imaging device 10 is of the "rapid exchange type," the inside of the outer sheath body 21 can remain hermetically sealed.

In accordance with an embodiment, the outer sheath body 21 houses the vibrator unit 40 (i.e., a vibrator), the inner sheath 30, and the drive shaft 50 in the outer sheath body 21. The vibrator unit 40, the inner sheath 30, and the drive shaft 50 in the outer sheath body 21 are movable along a central axis of the outer sheath body 21. In addition, the vibrator unit 40 and the drive shaft 50 in the outer sheath body 21 are rotatable in the outer sheath body 21. The outer sheath body 21 is a tubular body that is open only at a proximal end of the outer sheath body 21 and is not open, but closed, at a distal end of the outer sheath body 21. Note that the distal end of the outer sheath body 21 may be closed by another member. The outer sheath body 21 has a proximal portion fixed to the first housing 60.

The joint tube 23 is a tubular body that joins the distal tube 22 to the outer sheath body 21. The joint tube 23 has a distal portion surrounding the distal tube 22. The joint tube 23 has a proximal portion surrounding a distal portion of the outer sheath body 21. A central axis of the distal tube 22 and the central axis of the outer sheath body 21 are held out of alignment with each other, though they may be aligned with each other.

The inner sheath 30 is a tubular body having a portion on its distal side inserted in the outer sheath 20. The inner sheath 30 includes an inner sheath body 31 and an inner sheath reinforcing body 32. As illustrated in FIGS. 3A, 3B, 5A, and 5B, the inner sheath 30 includes a distal portion movably housed in the outer sheath body 21 for movement along the central axis of the outer sheath body 21. The inner sheath 30 includes a proximal portion extending to the proximal side from the outer sheath body 21 and the first housing 60 and being fixed to the second housing 70.

Figure 5A:
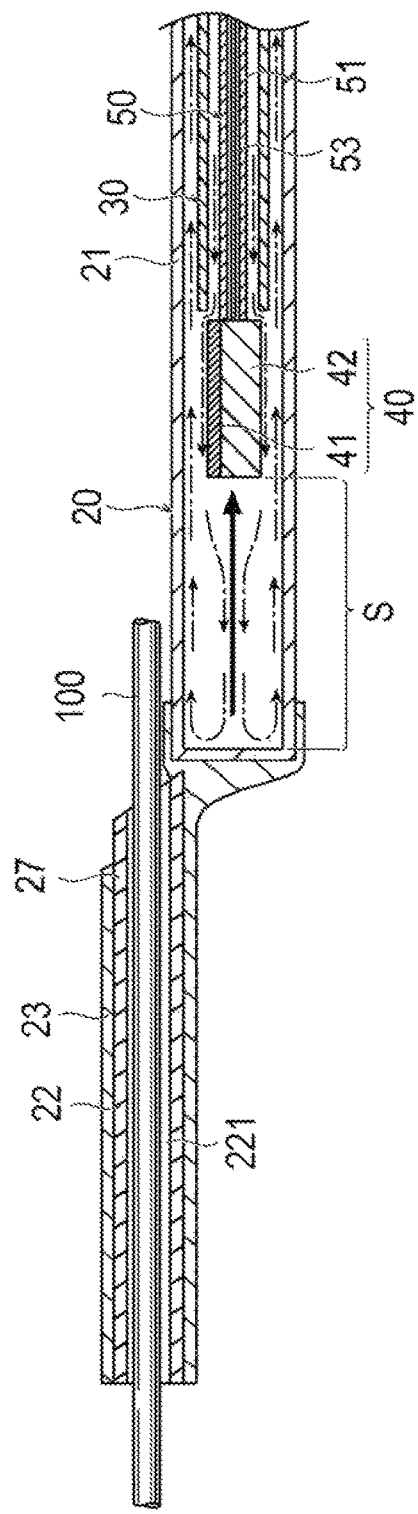
Figure 5B:
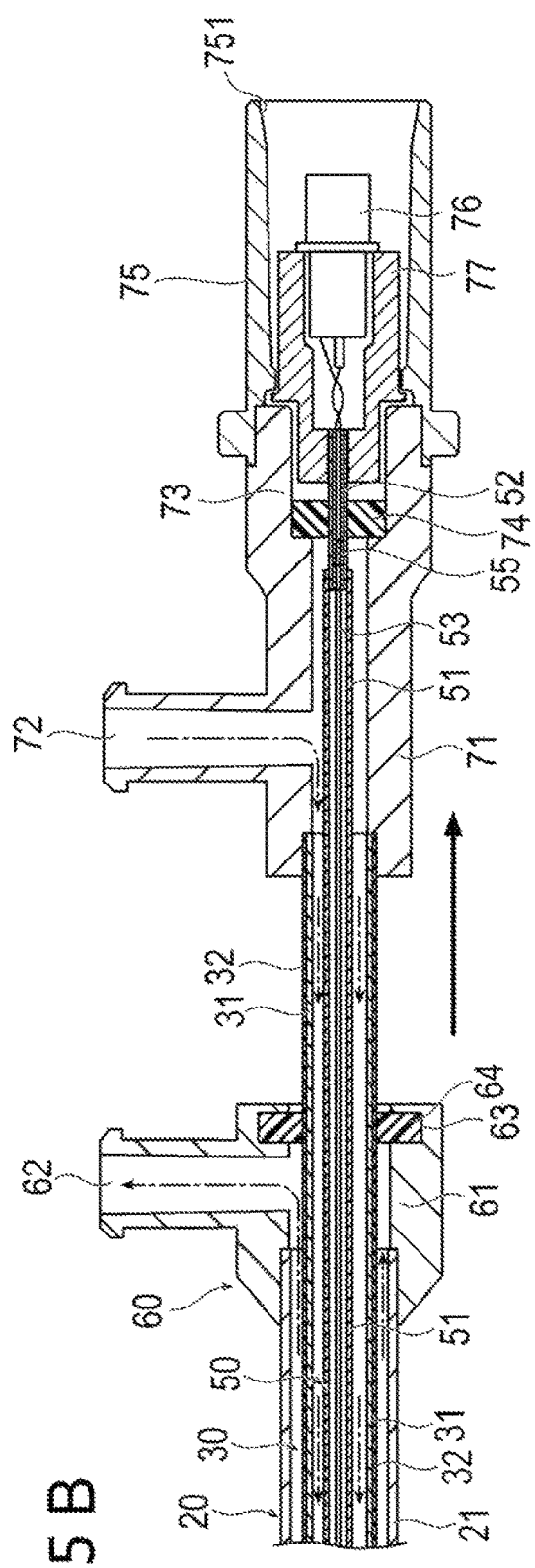

The inner sheath body 31 houses the drive shaft 50, and wherein the drive shaft 50 rotates within the inner sheath body 31. The inner sheath body 31 has a distal portion positioned relatively close to the vibrator unit 40 and proximal to the vibrator unit 40. The inner sheath reinforcing body 32 is a circular tube that reinforces the outer circumferential surface of a proximal portion of the inner sheath body 31. In accordance with an embodiment, an axial length of the inner sheath reinforcing body 32 is less than an axial length of the inner sheath body 31. The inner sheath reinforcing body 32 is disposed in a predetermined range where it is highly likely to be exposed more on the proximal side than the first housing 60. The inner sheath reinforcing body 32 increases a flexural rigidity of the inner sheath 30. Therefore, the proximal portion of the inner sheath 30 has a greater flexural rigidity than the distal portion of the inner sheath 30. Therefore, as illustrated in FIGS. 5A and 5B, the inner sheath 30 is unlikely to flex even when it is exposed more on the proximal side than the first housing 60. Consequently, the inner sheath 30 is stably movable reciprocally along a central axis of the outer sheath 20 with respect to the outer sheath 20. The inner sheath 30 can thus be pushed well into the first housing 60. The inner sheath reinforcing body 32 may be held in smooth contact with a first sealing portion 64. Note that the inner sheath reinforcing body may not be a circular tube. The inner sheath reinforcing body may be a filamentary material embedded in the inner sheath body 31, for example. The filamentary material should preferably, but not necessarily, be braided.

If the vibrator unit 40 is relatively large and spreads ultrasonic waves over long distances in order to acquire images in a wide space such as a heart chamber, an inside diameter of the outer sheath body 21 is also relatively large. It is not desirable to increase an outside diameter of the drive shaft 50 to match the large inside diameter of the outer sheath body 21 because the burden on a proximal portion of the drive shaft 50, rotational drive power required by the drive shaft 50, and an amount of heat generated with the rotational drive power are increased. However, if the outside diameter of the drive shaft 50 is excessively smaller than an outside diameter of the vibrator unit 40, a wide space is created between the inner circumferential surface of the outer sheath body 21 and the outer circumferential surface of the drive shaft 50. This wide space is responsible for making the drive shaft 50 unstable upon rotational and axial movement of the drive shaft 50. The inner sheath 30 is disposed in the wide space to make the drive shaft 50 stable upon rotational and axial movement. Note that the inner sheath 30 does not rotate with the drive shaft 50. Therefore, the rotational drive power required by the drive shaft 50 and the amount of heat generated with the rotational drive power are not increased.

The vibrator unit 40 sends ultrasonic waves to and receives ultrasonic waves from a lumen tissue. As illustrated in FIGS. 3A, 3B, 5A, and 5B, the vibrator unit 40 includes an ultrasonic vibrator 41 for sending and receiving ultrasonic waves and a holder 42 on which the ultrasonic vibrator 41 is disposed and which is fixed to the drive shaft 50. The maximum outer diameter of the vibrator unit 40 in a cross section perpendicular to a central axis of the drive shaft 50 is larger than the maximum outer diameter of a distal-side drive shaft 51. The maximum outer diameter of the vibrator unit 40 is substantially the same as the maximum outer diameter of the inner sheath 30, but is not limited to the maximum outer diameter of the vibrator unit 40 being substantially the same as the maximum outer diameter of the inner sheath 30.

The material of which the outer sheath body 21, the distal tube 22, the joint tube 23, and the inner sheath body 31 are made is not limited to any particular material insofar as it is flexible and has a certain level of mechanical strength. For example, the material of the outer sheath body 21, the distal tube 22, the joint tube 23, and the inner sheath body 31 should preferably be polyolefin such as polyethylene or polypropylene, polyester such as polyamide or polyethylene terephthalate, fluorine-based polymer such as PTFE (polytetrafluoroethylene) or ETFE (ethylene·tetrafluoro-ethylene copolymer), PEEK (polyether ether ketone), polyimide, or the like.

The material of which the inner sheath reinforcing body 32 is made is not limited to any particular material, but should preferably be stainless steel, polyimide, polyether ether ketone, or the like, for example.

The drive shaft 50 transmits rotational power to act from an external drive device 80 (see FIG. 2) to the vibrator unit 40. The drive shaft 50 includes a pliable distal-side drive shaft 51 that extends through the inner sheath 30 and a connection pipe 52 fixed to a proximal portion of the distal-side drive shaft 51. The distal-side drive shaft 51 has a distal end fixed to the holder 42. The distal-side drive shaft 51 is in the form of a tubular body of multilayer coils such as three-layer coils that are wound in alternate directions such as right, left, and right directions, for example. The connection pipe 52 may be a circular tube of metal, for example. The connection pipe 52 has a proximal portion fixed to a rotor 77 that is rotatable in the second housing 70. Signal wires 53 extend through the connection pipe 52. The signal wires 53 in the connection pipe 52 may be secured in place by a sealant 55 such as an adhesive. Therefore, a fluid cannot flow through the connection pipe 52.

When the drive shaft 50 transmits rotational power, the vibrator unit 40 is rotated for observing the internal structure of a tissue through 360° from a blood vessel or a heart chamber. The drive shaft 50 is movable along the central axis of the outer sheath body 21 in the outer sheath body 21.

The signal wires 53 are disposed so as to extend through the drive shaft 50. The signal wires 53 transmit signals from the rotor 77 to the vibrator unit 40. Furthermore, the signal wires 53 transmit signals detected by the vibrator unit 40 through the rotor 77 to the external drive device 80.

Figure 4:
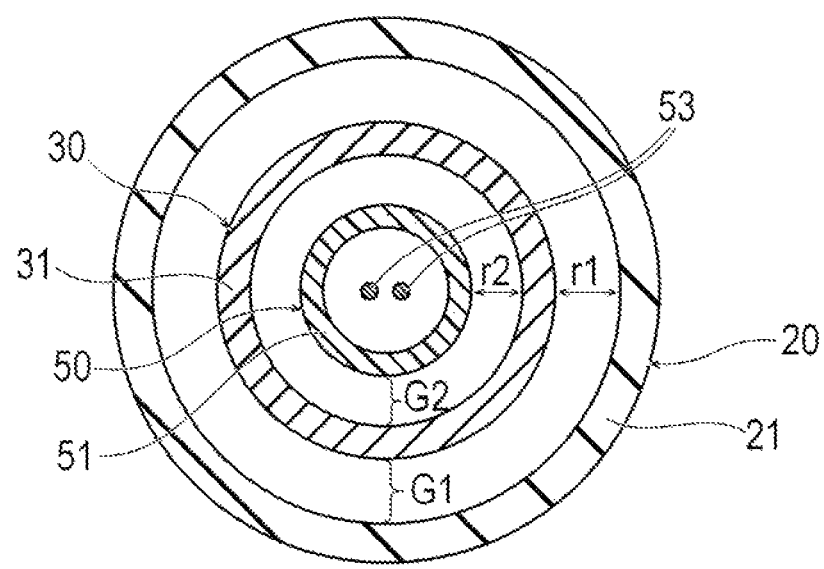
FIG. 4 is a cross-sectional view taken along line IV-IV of FIG. 3A.

As illustrated in FIG. 4, a first gap G1 is defined between the inner circumferential surface of the outer sheath 20 and the outer circumferential surface of the inner sheath 30. A second gap G2 is defined between the inner circumferential surface of the inner sheath 30 and the outer circumferential surface of the drive shaft 50. In a cross section perpendicular to the central axis of the inner sheath 30, the outer sheath 20, and the drive shaft 50, a cross-sectional area of the first gap G1 should preferably, but not necessarily, be larger than a cross-sectional area of the second gap G2. Moreover, a radial length r1 of the first gap G1 should preferably, but not necessarily, be larger than a radial length r2 of the second gap G2.

As illustrated in FIGS. 3A, 3B, 5A, and 5B, the outer sheath 20 has a proximal portion fixed to the first housing 60 in a fluid-tight fashion. The first housing 60 includes a first hollow portion 61 held in fluid communication with an inner lumen of the outer sheath 20, a first port 62, a first housing proximal portion 63, and the first sealing portion 64.

The first hollow portion 61 provides fluid communication between the first port 62 and the inner lumen of the outer sheath 20. The inner sheath 30 that leads out of the outer sheath 20 toward the proximal side and the drive shaft 50 extend through the first hollow portion 61. The first housing proximal portion 63 has a through hole held in fluid communication with the first hollow portion 61 and is positioned proximal to the first hollow portion 61. The first sealing portion 64 is disposed in the through hole in the first housing proximal portion 63. The inner sheath 30 and the drive shaft 50 extend through the first sealing portion 64. The first sealing portion 64 is held in slidable contact with the outer circumferential surface of the inner sheath 30 for sliding movement along the central axis of the inner sheath 30. The first sealing portion 64 provides a slidable seal between the first housing proximal portion 63 and the inner sheath 30. The first sealing portion 64 is not limited to any particular seal insofar as it is slidable against the outer circumferential surface of the inner sheath 30. For example, the first sealing portion 64 may be an O-ring or a cross-cut valve body. The cross-cut valve body is a valve body made of a pliable material in which a slit extending in one direction and another slit extending in another direction cross each other and the two slits are held in fluid communication with each other at their centers. The first port 62 is in the form of an opening to which a tube or the like for introducing or discharging a fluid such as a saline or saline solution can be interlocked.

The second housing 70 is disposed proximal to the first housing 60. The proximal portion of the inner sheath 30 that leads out of the first housing 60 toward the proximal side is fixed to the second housing 70 in a fluid-tight fashion. The second housing 70 is movable toward and away from the first housing 60 along the central axis of the inner sheath 30.

The second housing 70 includes a second hollow portion 71 held in fluid communication with an inner lumen of the inner sheath 30, a second port 72, a second housing proximal portion 73, and a second sealing portion 74. The second housing 70 further includes a joint 75, a connector 76, and the rotor 77.

The second hollow portion 71 provides fluid communication between the second port 72 and the inner lumen of the inner sheath 30. The drive shaft 50 that leads out of the inner sheath 30 toward the proximal side extends through the second hollow portion 71. The second housing proximal portion 73 has a through hole held in fluid communication with the second hollow portion 71 and is positioned proximal to the second hollow portion 71. The second sealing portion 74 is disposed in the through hole in the second housing proximal portion 73. The connection pipe 52 of the drive shaft 50 extends through the second sealing portion 74. The second sealing portion 74 is held in slidable contact with the outer circumferential surface of the connection pipe 52 for sliding movement in the direction in which the connection pipe 52 rotates. The second sealing portion 74 provides a slidable seal between the second housing proximal portion 73 and the drive shaft 50. The second sealing portion 74 is not limited to any particular seal insofar as it is slidable against the outer circumferential surface of the drive shaft 50. For example, the second sealing portion 74 may be an O-ring. The second port 72 is in the form of an opening to which a tube or the like for introducing or discharging a fluid such as saline can be interlocked.

The joint 75 is fixed to a proximal side of the second housing proximal portion 73. The joint 75 has a joint opening 751 defined in a proximal side of the joint 75 with the connector 76 and the rotor 77 disposed in the joint 75. The connector 76 can be interlocked with a drive connector 811 of the external drive device 80 (see FIG. 2) that enters the joint 75 via the joint opening 751. The connector 76 is mechanically and electrically interlocked with the drive connector 811. The signal wires 53 that extend through the connection pipe 52 are connected to the connector 76. Therefore, the connector 76 is connected to the vibrator unit 40 through the signal wires 53.

The connection pipe 52 is fixed to the rotor 77. The rotor 77 rotates in unison with the connector 76 within the joint 75. When the rotor 77 rotates, the drive shaft 50 fixed to the rotor 77 rotates. The rotor 77 is sandwiched between the joint 75 and the second housing proximal portion 73 to restrain the rotor 77 from moving axially. The rotor 77 is rotatable within the second housing 70 and movable together with the second housing 70 along a central axis of second housing 70. The vibrator unit 40 emits ultrasonic waves in response to a signal received through the connector 76 and the signal wires 53. Further, the vibrator unit 40 receives reflected waves, converts the reflected waves into a signal, and sends the signal through the signal wires 53 and the connector 76 to the external drive device 80. The external drive device 80 appropriately processes the received signal and displays the received signal as an image.

The material of which the first housing 60 and the second housing 70 are made is not limited to any particular material insofar as it has a certain level of mechanical strength. For example, the material of the first housing 60 and the second housing 70 should preferably be polycarbonate, polyamide, polysulfone, polyarylate, methacrylate-butylene-styrene copolymer, or the like.

Figure 2:
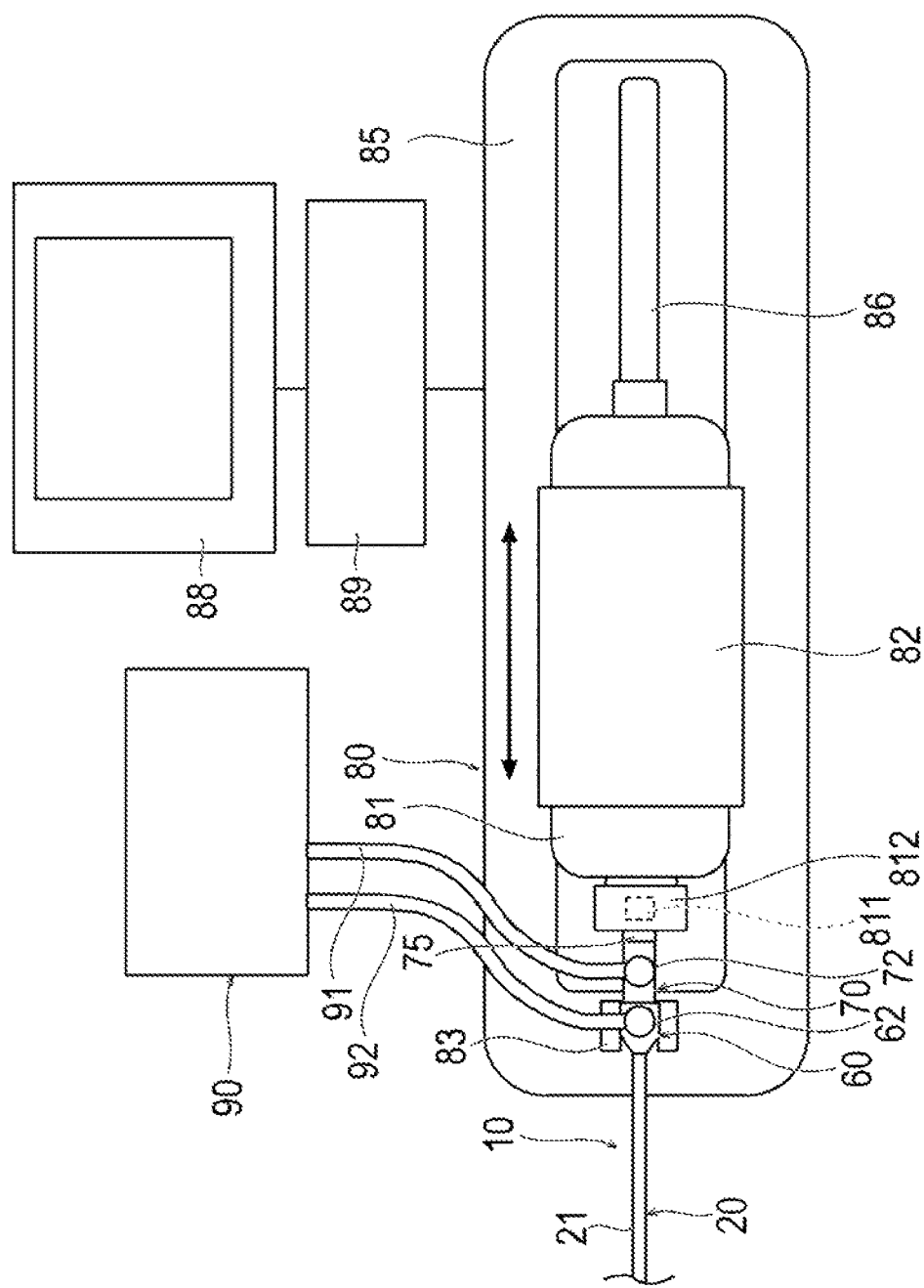
FIG. 2 is a schematic view of an imaging system incorporating the imaging device according to the embodiment.

As illustrated in FIG. 2, the imaging device 10 is connected to the external drive device 80 and the imaging device 10 is thereby driven. The external drive device 80 includes a driving portion 81 having a built-in drive source such as a motor for rotating the drive shaft 50, a moving portion 82 for moving the driving portion 81 in axial directions, and a support portion 83 supporting a portion of the imaging device 10 fixedly in position. The driving portion 81, the moving portion 82, and the support portion 83 are disposed on a base 85. The external drive device 80 is connected to a control portion 89 for controlling the driving portion 81 and the moving portion 82. Images obtained by the vibrator unit 40 are displayed on a display portion 88 connected to the control portion 89.

The moving portion 82 is capable of grasping and fixing the driving portion 81. The moving portion 82 may be, for example, a feed mechanism for driving the driving portion 81 with a drive source such as a motor. The moving portion 82 moves the fixed driving portion 81 back and forth along a groove rail 86 on the base 85.

The driving portion 81 includes the drive connector 811 that is connectable to the connector 76 of the imaging device 10 and a joint connecting portion 812 that is connectable to the joint 75 of the imaging device 10. When the connector 76 is connected to the drive connector 811, the driving portion 81 can send signals to and receive signals from the vibrator unit 40. Moreover, when the joint 75 is connected to the joint connecting portion 812, the drive shaft 50 can be rotated.

The imaging device 10 performs ultrasonic scanning by transmitting rotary motion of the driving portion 81 to the drive shaft 50 to rotate the vibrator unit 40 that is fixed to the distal end of the drive shaft 50, for scanning ultrasonic waves sent and received by the ultrasonic vibrator 41 substantially in radial directions. Further, the moving portion 82 can pull the drive shaft 50 toward the proximal side, for moving the ultrasonic vibrator 41 toward the proximal side while rotating the ultrasonic vibrator 41. Consequently, the imaging device 10 is able to obtain a sectional image, scanned through 360°, of a surrounding tissue of a blood vessel or a heart chamber along the central axis of the outer sheath 20 up to a desired position.

The imaging device 10 is connected to a pump device 90. The pump device 90 is able to circulate a fluid. The pump device 90 includes a supply tube 91 for supplying the fluid and a retrieval tube 92 for retrieving the fluid. The supply tube 91 is connected to the second port 72. The retrieval tube 92 is connected to the first port 62. The pump device 90 includes a pump mechanism that is not limited to any particular pump mechanism, but may be a peristaltic pump, a centrifugal pump, a diaphragm pump, or the like. Note that the pump device 90 may be of a non-circulating type. In a case where the pump device 90 is of the non-circulating type, the first port 62 is connected to a tube leading to a waste container.

Next, a process of observing a biotissue from a lumen in a living body using the imaging device 10 according to the present embodiment will be described below.

First, before the imaging device 10 is inserted into the lumen in the living body, the supply tube 91 of the pump device 90 is connected to the second port 72, and the retrieval tube 92 of the pump device 90 is connected to the first port 62.

Then, the second housing 70 is brought closest to the first housing 60, as illustrated in FIGS. 1, 3A, and 3B. At this time, the vibrator unit 40 is positioned in the vicinity of the distal end of the outer sheath body 21. The distal end of the inner sheath 30 is positioned relatively close to the vibrator unit 40 on the proximal side of the vibrator unit 40. The distal end of the inner sheath 30 is relatively close to the distal end of the drive shaft 50. Since the inner sheath 30 thus covers the drive shaft 50 substantially over an entire length of the drive shaft 50, the drive shaft 50 rotates stably when the drive shaft 50 drives the vibrator unit 40, allowing signals to be received and images to be acquired with relatively high accuracy. Moreover, a distance between the distal end of the outer sheath 20 and the distal end of the inner sheath 30 is just substantially enough to have the vibrator unit 40 disposed in the distance between the distal end of the outer sheath 20 and the distal end of the inner sheath 30. When a fluid such as saline is introduced, the distance makes it relatively easy to remove air from the distal portion of the outer sheath 20.

Next, the pump device 90 is driven to introduce a fluid, for example, saline, from the second port 72 of the second housing 70 into the second hollow portion 71 of the second housing 70. The saline flows into the second gap G2 between the drive shaft 50 and the inner sheath 30, as indicated by the dot-and-dash lines in FIGS. 3A and 3B. Note that the drive shaft 50 rotatably extends through the second housing 70. However, the second sealing portion 74 provides a seal between the second housing 70 and the drive shaft 50. Therefore, the saline does not leak out from between the second housing 70 and the drive shaft 50. Consequently, the saline is effectively led into the inner sheath 30. The saline that is introduced into the second gap G2 between the inner sheath 30 and the drive shaft 50 moves in the second gap G2 toward the distal side and reaches farther on the distal side than the inner sheath 30. The space between the outer sheath 20 and the vibrator unit 40 is thus filled up with the saline. The distal portion of the outer sheath body 21 is not open, and is closed. Therefore, the saline is not discharged from the distal portion of the outer sheath body 21.

Next, the saline flows from the distal side of the inner sheath 30 into the first gap G1 between the outer sheath 20 and the inner sheath 30 and moves toward the proximal side. Thereafter, the saline flows into the first hollow portion 61 of the first housing 60. Note that the inner sheath 30 extends movably through the first housing 60 for movement along the central axis of the first housing 60. However, the first sealing portion 64 provides a seal between the first housing 60 and the inner sheath 30. Therefore, the saline does not leak out from between the first housing 60 and the inner sheath 30. Consequently, the saline is effectively discharged from the first port 62. Air in the imaging device 10 is thus removed, and the space around the vibrator unit 40 is filled up with the saline.

Next, with the pump device 90 continuing or stopping circulating the saline, the imaging device 10 is inserted into the lumen in the living body. Thereafter, as illustrated in FIG. 2, the imaging device 10 is interlocked with the external drive device 80. Specifically, the joint 75 (see FIGS. 3A and 3B) of the imaging device 10 is connected to the joint connecting portion 812 of the driving portion 81, thereby making it possible to send and receive signals between the vibrator unit 40 and the external drive device 80. Furthermore, the drive shaft 50 can be rotated and moved by the driving portion 81 and the moving portion 82. Then, the first housing 60 is fitted into the support portion 83.

Next, the guide wire 100 is inserted percutaneously into a femoral artery or vein or the like. The guide wire 100 inserted in the blood vessel is then put through the guide wire lumen 221 of the imaging device 10, and the imaging device 10 is pushed ahead along the guide wire 100. Preceded by the guide wire 100, the imaging device 10 is moved into the heart chamber, for example.

Next, as illustrated in FIGS. 5A and 5B, a pull-back operation is performed while the external drive device 80 is rotating the drive shaft 50 with image data being acquired from the vibrator unit 40. The pull-back operation is carried out when the moving portion 82 connected to the proximal portion of the imaging device 10 is operated by the control portion 89. The acquired data is digitally processed by the control portion 89 and displayed as image data on the display portion 88 (see FIG. 2). The display portion 88 can display the image data substantially in real time.

After the imaging device 10 has been inserted in the living body, the pump device 90 is driven when necessary or continuously to introduce the saline into the second port 72 of the second housing 70. The supplied saline passes through the second gap G2 and the first gap G1 and the saline is discharged from the first port 62. Therefore, foreign matter such as air deposited on the vibrator unit 40, for example, is removed from the first port 62 rather than being discharged into the living body. The vibrator unit 40 can thus efficiently send and receive ultrasonic waves via the saline that fills the outer sheath body 21.

As described above, the imaging device 10 according to the present embodiment has the elongated outer sheath 20, the drive shaft 50 to which the vibrator unit 40, i.e., the vibrator, disposed in the outer sheath 20 is fixed, for transmitting drive power to the vibrator unit 40 in the outer sheath 20, the inner sheath 30 that is movable along the central axis of the outer sheath 20 in the outer sheath 20, the drive shaft 50 extending through the inner sheath 30, the first housing 60 to which the proximal portion of the outer sheath 20 is fixed, the drive shaft 50 and the inner sheath 30 extending through the first housing 60, and the second housing 70 that is disposed on proximal to the first housing 60 and to which the proximal portion of the inner sheath 30 is fixed, the drive shaft 50 being rotatably held in the second housing 70. The imaging device 10 also has the first gap G1 between the inner sheath 30 and the outer sheath 20, and the second gap G2 between the inner sheath 30 and the drive shaft 50. The first gap G1 and the second gap G2 are held in fluid communication with each other on the distal side of the inner sheath 30. The first housing 60 has the first port 62 held in fluid communication with the first gap G1, and the second housing 70 is movable toward and away from the first housing 60 and has the second port 72 held in fluid communication with the second gap G2.

The imaging device 10 constructed as described above allows the fluid to flow between the first port 62 and the second port 72 that are movable relatively to each other, using the first gap G1 and the second gap G2. The fluid passes through the second gap G2 and reaches the distal side of the inner sheath 30, thereafter passing through the first gap G1 and being discharged. Therefore, the imaging device 10 is able to effectively supply the fluid to the vibrator unit 40 positioned distal to the inner sheath 30 at any desired timings while making the vibrator unit 40 movable along the central axis of the outer sheath 20 in the outer sheath 20. Consequently, the imaging device 10 is capable of stably acquiring images in a wide range with the vibrator unit 40 moving in the outer sheath 20 and effectively supplying the fluid to the vibrator unit 40, to acquire relatively highly accurate three-dimensional images. The inner sheath 30 is disposed between the outer sheath 20 and the drive shaft 50 and allows the drive shaft 50 to be driven in an appropriate clearance. Therefore, the inner sheath 30 makes the drive shaft 50 to be stable upon rotational and axial movement of the drive shaft 50. Consequently, even if the vibrator unit 40 is large and spreads ultrasonic waves over long distances and the inside diameter of the outer sheath 20 is large accordingly, the inner sheath 30 appropriately reduces the wide space created between the outer sheath 20 and the drive shaft 50.

Further, the first housing 60 has the first sealing portion 64 held in slidable contact with the outer circumferential surface of the inner sheath 30 for sliding movement along the central axis of the inner sheath 30 and providing a seal between the first housing 60 and the inner sheath 30, and the second housing 70 has the second sealing portion 74 held in slidable contact with the outer circumferential surface of the drive shaft 50 for sliding movement in the circumferential direction of the drive shaft 50 and providing a seal between the second housing 70 and the drive shaft 50. Therefore, the fluid is restrained from leaking out of the first housing 60 and the second housing 70. The fluid can thus be effectively introduced into the imaging device 10.

Moreover, the distal end of the inner sheath 30 is close to the distal end of the drive shaft 50. Therefore, the inner sheath 30 surrounds the drive shaft 50 up to a position close to the distal end of the drive shaft 50. The fluid can thus be well supplied to the gap between the outer sheath 20 and the vibrator unit 40. The drive shaft 50 is supported by the inner sheath 30 and is stably rotatable in the inner sheath 30. The imaging device 10 can therefore acquire relatively highly accurate three-dimensional images.

Further, the diameter of the inner sheath 30 is smaller than the maximum outside diameter of the vibrator unit 40, i.e., the vibrator. The vibrator unit 40 can thus push the fluid to cause the fluid to flow into the first gap G1. Therefore, it is relatively easy to remove air trapped in the outer sheath 20.

Further, in the cross section perpendicular to the central axis of the inner sheath 30, the cross-sectional area of the second gap G2 is larger than the cross-sectional area of the first gap G1. Therefore, the cross-sectional area of the first gap G1 close to the first port 62 is larger than the cross-sectional area of the second gap G2 close to the second port 72. When the fluid is supplied to the second port 72 and discharged from the first port 62, the fluid passes through the second gap G2 that has a larger fluid channel resistance and thereafter passes through the first gap G1 that has a smaller fluid channel resistance. Therefore, the fluid channel resistance is lower downstream, reducing the pressure required to cause the fluid to pass. Accordingly, the flowability of the fluid increases.

Further, in the cross section perpendicular to the central axis of the inner sheath 30, the radial length r1 of the first gap G1 is longer than the radial length r2 of the second gap G2. Therefore, the cross-sectional area of the first gap G1 that is positioned radially outwardly of the second gap G2 is easily made larger than the cross-sectional area of the second gap G2. As the second gap G2 between the inner sheath 30 and the drive shaft 50 is smaller, the drive shaft 50 can be rotated stably in the inner sheath 30. Therefore, the imaging device 10 can acquire relatively highly accurate three-dimensional images.

Further, the distal portion of the inner lumen of the outer sheath 20 is closed. The fluid that is supplied from the first port 62 or the second port 72 is thus prevented from being discharged, together with foreign matter such as air, into the living body.

Further, the proximal portion of the inner sheath 30 has a greater flexural rigidity than the distal portion of the inner sheath 30. Therefore, the proximal portion of the inner sheath 30 is unlikely to flex even when it is exposed more on the proximal side than the first housing 60. Consequently, the inner sheath 30 is stably movable reciprocally along the central axis of the outer sheath 20 with respect to the outer sheath 20.

Furthermore, the first housing 60 is fixed to the support portion 83 that fixes the position of the first housing 60, and the second housing 70 is fixed to the moving portion 82 that can be moved axially reciprocally with respect to the support portion 83. When the moving portion 82 moves reciprocally with respect to the support portion 83, the second housing 70 moves reciprocally with respect to the first housing 60. Therefore, the first housing 60 and the second housing 70 are reciprocally movable by being fixed to the support portion 83 and the moving portion 82, respectively.

If the vibrator unit 40 were not moved, it would be difficult to remove air trapped between the distal end of the outer sheath 20 and the distal end of the ultrasonic vibrator 41. However, when the vibrator unit 40 is moved from the position illustrated in FIGS. 5A and 5B to the position illustrated in FIGS. 3A and 3B, the saline that fills up a distal space portion S (see FIGS. 5A and 5B) between the distal end of the outer sheath 20 and the distal end of the ultrasonic vibrator 41 moves toward the proximal side. At this time, a volume of saline that is as large as the vibrator unit 40, etc. starts to move into the first gap G1. Therefore, a fluid flow occurs into the first gap G1, making it relatively easy to remove air trapped in the distal space portion S. As the maximum outside diameter of the vibrator unit 40 is larger than the outside diameter of the inner sheath 30, the vibrator unit 40 is relatively effective to push out the fluid. Note that the saline is appropriately added from the second port 72. When the vibrator unit 40 is moved from the position illustrated in FIGS. 3A and 3B to the position illustrated in FIGS. 5A and 5B, the vibrator unit 40 draws air that is trapped in the distal space portion S and does not move into the first gap G1 toward the proximal side of the vibrator unit 40. Therefore, air is removed from around the vibrator unit 40 and is hence prevented from obstructing ultrasonic waves as they are sent from and received by the vibrator unit 40. Further, when the second housing 70 is moved reciprocally, the vibrator unit 40 is also moved reciprocally. As a consequence, air is effectively removed from around the vibrator unit 40 by repeating the reciprocating movement of the vibrator unit 40.

Furthermore, since the maximum outer diameter of the imaging unit, for example, which includes the vibrator unit 40, is larger than the inner diameter of the inner sheath 30, the saline that flows out of the first gap G1 impinges upon the distal end of the vibrator unit 40 and is liable to flow from the first gap G1 in a direction opposite the flow. Therefore, a flow of the saline from the first gap G1 into the second gap G2 is apt to occur, rather effectively removing air trapped in the second gap G2.

The vibrator unit 40 and the inner sheath 30 can be pulled out of the outer sheath 20 by moving the second port 72 toward the proximal side over a distance that is as long as the length of the inner sheath 30. In other words, the vibrator unit 40 and the inner sheath 30 can be replaced. Accordingly, when a need arises, a vibrator unit 40 having a different frequency and an inner sheath 30 may be inserted into the outer sheath 20. For example, while the imaging device 10 remains in the living body, the vibrator unit 40 and the inner sheath 30 may be pulled out, leaving the outer sheath 20 behind in the living body. Outside of the living body, the outer sheath 20 may be changed while the vibrator unit 40 and the inner sheath 30 remain unchanged. In other words, a suitable outer sheath 20 can be selected depending on the application in which it is used or the body region on which it is used. For example, for use in a right atrium, since it is not necessary to follow an intricately curved duct, an outer sheath free of a guide wire lumen, i.e., an outer sheath free of the distal tube 22 and the joint tube 23 according to aforesaid embodiment, is used. For use in a left atrium, since it is necessary to follow an intricately curved duct, an outer sheath 20 with a guide wire lumen is used.

Note that the present disclosure is not limited to the embodiment described above. Various changes and modifications may be made therein by those skilled in the art within the technical idea of the present disclosure. For example, according to aforesaid embodiment, the present disclosure is applied to an ultrasonic catheter. However, the present disclosure is also applicable to devices that use light, such as an optical interference tomography diagnostic apparatus (OCT: Optical Coherence Tomography) and an optical frequency domain imaging diagnostic apparatus (OFDI: Optical Frequency Domain Imaging), and endoscopes or the like.

The optical interference tomography diagnostic apparatus and the optical frequency domain imaging diagnostic apparatus include an imaging core unit as an imaging unit for emitting light toward an inner lumen surface of a blood vessel and detected reflected light from the inner lumen surface of the blood vessel.

The endoscopes include a CCD (Charge-Coupled Device) sensor or a CMOS (Complementary Metal-Oxide Semiconductor) sensor as an imaging unit. The imaging unit has lenses and a photodetector unit, receives external light from a subject with the photodetector unit, and converts the received light into an electric signal representing the intensity of the light.

According to the embodiment described above, the fluid is supplied from the second port 72. However, the fluid may be supplied from the first port 62 and discharged from the second port 72. In this case, the cross-sectional area of the first gap G1 should preferably, but not necessarily, be smaller than the cross-sectional area of the second gap G2. Moreover, the radial length r1 of the first gap G1 should preferably, but not necessarily, be smaller than the radial length r2 of the second gap G2.

The detailed description above describes embodiments of an imaging device and more particularly to an imaging device for acquiring images by being inserted into a lumen such as a blood vessel or a duct. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging device comprising:
   an elongated outer sheath;
   an imaging unit disposed in the outer sheath;
   a drive shaft to which the imaging unit is fixed at a distal portion of the drive shaft, the drive shaft configured to transmit drive power to the imaging unit in the outer sheath;
   an inner sheath configured to be movable along a central axis of the outer sheath in the outer sheath, the drive shaft extending through the inner sheath;
   a first housing to which a proximal portion of the outer sheath is fixed, the drive shaft and the inner sheath extending through the first housing;
   a second housing that is disposed proximal to the first housing and to which a proximal portion of the inner sheath is fixed, the drive shaft being rotatably held in the second housing;
   a first gap between the inner sheath and the outer sheath;
   a second gap between the inner sheath and the drive shaft;
   the first housing including a first port held in fluid communication with the first gap, the first port configured to introduce a fluid into the first gap from outside of the imaging device or discharge the fluid from the first gap to the outside of the imaging device;
   the second housing is configured to be movable toward and away from the first housing and includes a port held in fluid communication with the second gap, the port configured to introduce the fluid into the second gap from the outside of the imaging device or discharge the fluid from the second gap to the outside of the imaging device, the inner sheath including an open distal end; and
   wherein the drive shaft is configured to pass through the open distal end of the inner sheath, and the imaging unit fixed to the distal portion of the drive shaft is disposed apart from the open distal end of the inner sheath so as to form fluid communication between the first gap and the second gap at the open distal end of the inner sheath.

2. The imaging device according to claim 1, wherein
   the first housing includes a first sealing portion held in slidable contact with an outer circumferential surface of the inner sheath for sliding movement along a central axis of the inner sheath and providing a seal between the first housing and the inner sheath; and
   the second housing includes a second sealing portion held in slidable contact with an outer circumferential surface of the drive shaft for sliding movement in a circumferential direction of the drive shaft and providing a seal between the second housing and the drive shaft.

3. The imaging device according to claim 1, wherein the open distal end of the inner sheath is distal to a distal end of the drive shaft.

4. The imaging device according to claim 1, wherein a maximum outer diameter of the imaging unit is larger than an inner diameter of the inner sheath.

5. The imaging device according to claim 1, wherein a cross-sectional area of the first gap is larger than a cross-sectional area of the second gap in a cross section perpendicular to the central axis of the inner sheath.

6. The imaging device according to claim 1, wherein a radial length of the first gap is longer than a radial length of the second gap in a cross section perpendicular to the central axis of the inner sheath.

7. The imaging device according to claim 1, wherein the outer sheath has a distal portion that includes a closed inner lumen.

8. The imaging device according to claim 1, wherein the proximal portion of the inner sheath has a greater flexural rigidity than a distal portion of the inner sheath.

9. The imaging device according to claim 1, wherein
the first housing is fixed to a support portion that fixes a position of the first housing;
the second housing is fixed to a moving portion, the moving portion configured to be moved axially reciprocally with respect to the support portion; and
when the moving portion moves reciprocally with respect to the support portion, the second housing moves reciprocally with respect to the first housing.

10. The imaging device according to claim 1, when the second housing is configured to move toward and away from the first housing, and wherein the imaging unit is kept apart from of the open distal end of the inner sheath.

11. The imaging device according to claim 1, wherein signal wires extend through an inside of the drive shaft to the imaging wire and the signal wires are configured to transmit signals to the imaging unit and transmit signals detected by the imaging unit.

12. The imaging device according to claim 1, wherein the drive shaft is configured to rotate within the inner sheath, wherein the inner sheath does not rotate with the drive shaft when the drive shaft rotates within the inner sheath.

13. A method of removing air from the imaging device according to claim 1, the method comprising:
introducing the fluid which comprises a saline solution into a proximal side of the imaging device;
flowing the saline solution in the second gap between the inner sheath and the drive shaft from the proximal side of the imaging device towards a distal side of the imaging device; and
filling a space between the outer sheath and the imaging unit with the saline solution from between the inner sheath and the drive shaft to remove the air from the imaging device.

14. The method according to claim 13, further comprising:
flowing the saline solution from the space between the outer sheath and the imaging unit to the proximal side of the imaging device in the first gap between the outer sheath and the inner sheath.

15. The method according to claim 13, further comprising:
attaching proximal portion of the outer sheath to the first housing and extending the drive shaft and the inner sheath through the first housing; and
disposing the second housing proximal to the first housing and fixing proximal portion of the inner sheath to the second housing, the drive shaft being rotatably held in the second housing.

16. The method according to claim 15, further comprising:
connecting a retrieval tube of a pump device to the first port of the first housing;
connecting a supply tube of the pump device to the second port of the second housing; and
moving the second housing toward and away from the first housing.

17. An imaging device comprising:
an elongated outer sheath;
an imaging unit disposed in the outer sheath;
a drive shaft to which the imaging unit is fixed at a distal portion of the drive shaft, the drive shaft configured to transmit drive power to the imaging unit in the outer sheath;
an inner sheath configured to be movable along a central axis of the outer sheath in the outer sheath, the drive shaft extending through the inner sheath;
a first housing to which a proximal portion of the outer sheath is fixed, the drive shaft and the inner sheath extending through the first housing;
a second housing that is disposed proximal to the first housing and to which a proximal portion of the inner sheath is fixed, the drive shaft being rotatably held in the second housing;
a first gap between the inner sheath and the outer sheath;
a second gap between the inner sheath and the drive shaft, wherein the first housing has a first port held in fluid communication with the first gap;
the second housing configured to be movable toward and away from the first housing and includes a port held in fluid communication with the second gap;
the inner sheath including a distal opening at a distal end of the inner sheath, the distal opening held in fluid communication with the second gap;
the imaging unit being disposed apart from the distal end of the inner sheath to define a third gap between the imaging unit and the distal opening of the inner sheath, the third gap held in fluid communication with the first gap and the second gap at the distal end of the inner sheath; and
when the second housing moves toward and away from the first housing, the inner sheath moves with the imaging unit along the central axis of the outer sheath in the outer sheath while keeping the third gap.

18. The imaging device according to claim 17, wherein
the first housing includes a first sealing portion held in slidable contact with an outer circumferential surface of the inner sheath for sliding movement along a central axis of the inner sheath and providing a seal between the first housing and the inner sheath; and
the second housing includes a second sealing portion held in slidable contact with an outer circumferential surface of the drive shaft for sliding movement in a circumferential direction of the drive shaft and providing a seal between the second housing and the drive shaft.

19. The imaging device according to claim 17, wherein signal wires extend through an inside of the drive shaft to the imaging wire and the signal wires are configured to transmit signals to the imaging unit and transmit signals detected by the imaging unit.

20. The imaging device according to claim 17, wherein the drive shaft is configured to rotate within the inner sheath, and the inner sheath does not rotate with the drive shaft when the drive shaft rotates within the inner sheath.

* * * * *